United States Patent [19]

Kikumoto et al.

[11] 4,060,641

[45] Nov. 29, 1977

[54] PHARMACEUTICALLY ACTIVE 2-(3-ALKYLAMINOPROPOXY)DI-PHENYLMETHANES

[75] Inventors: Ryoji Kikumoto, Machida; Akihiro Tobe, Kawasaki; Shinji Tonomura, Tokyo; Hidenobu Ikoma, Kawasaki, all of Japan

[73] Assignee: Mitsubishi Chemical Industries Ltd., Tokyo, Japan

[21] Appl. No.: 734,521

[22] Filed: Oct. 21, 1976

Related U.S. Application Data

[62] Division of Ser. No. 635,147, Nov. 25, 1975, Pat. No. 4,024,282.

[51] Int. Cl.$^2$ .................. A01N 9/20; A01N 9/24; C07C 93/06

[52] U.S. Cl. .................... 424/330; 424/316; 260/297 R; 260/501.18; 260/501.19; 260/570 R; 544/106

[58] Field of Search .......... 260/570 R, 501.18, 501.19; 424/316, 330

[56] References Cited

U.S. PATENT DOCUMENTS

| 2,703,324 | 3/1955 | Binkley et al. | 260/570 X |
| 3,121,724 | 2/1964 | Shapiro et al. | 260/570.7 X |

*Primary Examiner*—Robert V. Hines
*Attorney, Agent, or Firm*—Oblon, Fisher, Spivak, McClelland & Maier

[57] ABSTRACT

2-(3-Alkylaminopropoxy) diphenylmethanes have been produced and have been found to possess antidepressant activity.

4 Claims, No Drawings

PHARMACEUTICALLY ACTIVE 2-(3-ALKYLAMINOPROPOXY)DIPHENYLMETHANES

This is a division of application Ser. No. 635,147, filed Nov. 25, 1975, and now U.S. Pat. No. 4,024,282.

BACKGROUND OF THE INVENTION

1. Field of the Invention

This invention relates to 2-(3-alkylaminopropoxy) diphenylmethanes which are pharmacologically active as antidepressants.

2. Description of the Prior Art

L. C. Cheney et al, J. AM.CHEM.SOC., Vol. 71, 60–64 (1949) describes several diphenylmethanes containing a substituent at the 2-position, including 2-dimethylaminoethoxy, 2-diethylaminoethoxy, 2-morpholinoethoxy, 2-(1-piperidyl) ethoxy, 2-isopropylaminoethoxy, 3-(1-piperidyl) propoxy, 3-dimethylaminopropoxy and 3-dibutylaminopropoxy. That reference also indicates that 2-(2-aminoethoxy)-diphenylmethanes and 2-(3-aminopropoxy) diphenylmethanes have antihistaminic and local anesthetic activity in animals. However, it is to be noted that the 2-(3-alkylaminopropoxy)-diphenylmethanes of this invention are not described in that reference. It is also noted that there is no indication in that reference that the 2-(3-alkylaminopropoxy) diphenylmethanes possess antidepressant activity. As a matter of fact, the 2-(3-dimethylaminopropoxy)-diphenylmethane and 2-(2-dimethylaminoethoxy) diphenylmethane which are described in that reference and 2-(2-methylaminoethoxy) diphenylmethane do not possess antidepressant activity according to pharmacological testing.

SUMMARY OF THE INVENTION

This invention relates to compounds of the formula (I):

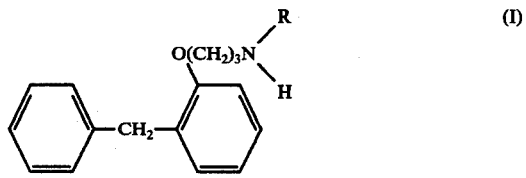

wherein R is $C_1$–$C_5$ alkyl and to the pharmaceutically acceptable acid addition salts of said compound.

This invention also relates to a method for palliating conditions of depression in warm-blooded mammals which comprises administering to said mammal in need of treatment an antidepressant effective amount of a compound of Formula I. The said compound is produced by reacting a 2-(3-halogenopropoxy) diphenylmethane of the formula (II):

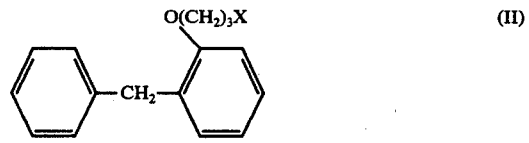

wherein X is halogen, with an amine of the formula (III):

R—NH$_2$         (III)

wherein R is as defined above.

DESCRIPTION OF THE INVENTION

As summarized above, this invention relates to a group of compounds useful as pharmaceutical agents, which compounds are represented by Formula I above.

Illustrative of the compounds of this invention are the following:

2-(3-methylaminopropoxy) diphenylmethane
2-(3-ethylaminopropoxy) diphenylmethane The pharmaceutically acceptable acid addition salts of the above compounds are, of course, also included within the scope of this invention. It will be understood that the term "pharmaceutically acceptable acid addition salts" as used herein is intended to include non-toxic salts of the compounds of this invention with an anion. Representative of such salts are hydrochlorides, hydrobromides, sulfates, phosphates, nitrates, acetates, succinates, adipates, propionates, tartrates, maleates, citrates, benzoates, toluenesulfonates, and methanesulfonates.

The 2-(3-methylaminopropoxy) diphenylmethane is most preferred due to its high level of antidepressant activity and to its low level of toxicity.

PREPARATION

The compounds of this invention are prepared by reacting an 2-(3-halogenopropoxy) diphenylmethane with an amine. The 2-(3-halogenopropoxy) diphenylmethane starting materials which are represented by Formula II above can be prepared by reacting 2-hydroxydiphenylmethane with a 1,3-dihalogenopropane in the presence of an alkali. The amine starting materials which are represented by Formula III above include primary amines, such as methylamine, ethylamine, isopropylamine or the like. The amine reacts with an equimolecular amount of the 2-(3-halogenopropoxy) diphenylmethane. However, the use of excess amine will tend to accelerate the reaction. Normally, the amount of amine used will be in the range of 1 to 100 moles per 1 mole of the 2-(3-halogenopropoxy)-diphenylmethane.

The reaction can be carried out without the addition of a solvent. However, the use of a reaction-inert solvent will enhance the possibility of a more homogenous reaction. Examples of suitable solvents include water, dioxane, tetrahydrofuran, dimethyl sulfoxide, lower aliphatic alcohols or a mixture thereof.

The reaction temperature is not critical, but normally will range from room temperature to 150° C. The reaction time will vary widely with the reaction temperature, and the reactivity of the starting materials, but normally will be in the range of from 10 minutes to 40 hours.

The presence of bases which neutralize a hydrogen halide formed in the course of the reaction will have an accelerating effect on the reaction. Examples of suitable bases are the inorganic bases, such as potassium hydroxide, sodium hydroxide, potassium carbonate, sodium carbonate or the like; and tertiary amines, such as pyridine, triethylamine or the like.

The amount of base used will normally be within the range of 1 to 5 moles per one mole of the 2-(3-halogenopropoxy)-diphenylmethane. When a base is absent, the 2-(3-alkylaminopropoxy) diphenylmethanes will react with hydrogen halide formed during the reaction, and will be converted to the corresponding acid addition salts. Acid addition salts of the 2-(3-alkylaminopropoxy) diphenylmethanes may also be conveniently prepared by contacting the compounds with a suitable acid. The 2-(3-alkylaminopropoxy) diphenylmethanes and the acid addition salts thereof may be purified by recrystallization employing a suitable solvent such as alcoholether.

Pharmacological testing of the 2-(3-alkylaminopropoxy)diphenylmethanes has demonstrated that they are useful as antidepressant agents, as evidenced by their ability to reverse reserpine hypothermia in mice. Anticonvulsant activity has also been found in the compounds of this invention.

The compounds have been tested in mice for antidepressant, sedative, anticonvulsant and anticholinergic activity.

The compounds were administered intraperitoneally and the activities of the compounds were compared with those of Amitriptyline. Antidepressant activity was evaluated by antagonism of reserpine (5 mg/kg i.p.) induced hypothermia (P. S. J. Spencer in "Antidepressant Drugs" S. Garattini and M. N. G. Duhes, ed., Excerpta Medica Foundation, Amsterdam, pages 194-204 (1967)) and antireserpine activity was expressed as relative potency (Amitriptyline = 1).

LD50 was calculated by Litchfield-Wilcoxon method.

CNS depressant activity was defined by the ability of the compounds to cause neurological deficit as measured by traction tests (S. Courvoisier, R. Ducrot, L. Julou; "Psychotropic Drugs" ed. by S. Garattini, V. Ghetti, page 373, (1957)) and spontaneous motor activity (Spontaneous motor activity was measured by ANIMEX apparatus).

Anticonvulsant activity was determined by antagonism of electroshock induced tonic extensor (L. S. Goodman, M. Singh Grewal, W. C. Brown and E. A. Swinyard, J. Pharmacol, Exptal. Therap., 108, 168 (1953)).

Central anticholinergic effect was assessed by testing the tremorine induced tremor in mice (G. M. Everett, L. E. Bloucus and J. M. Sheppard, Science 124 79 (1956)).

Results are summarized in Table I and Table II, in which ED50 is defined as the dose of the test compounds, which prevent 50% of each response.

Table I

| Antireserpine Activity in Mice | | |
|---|---|---|
| Compound | Relative Potency | LD50 (mg/kg i.p.) |
| 2-(3-methylaminopropoxy) diphenylmethane hydrochloride | 0.56 | 160 |
| 2-(3-dimethylaminopropoxy) diphenylmethane hydrochloride | 0.00 | — |
| 2-(2-dimethylaminoethoxy) diphenylmethane hydrochloride | 0.00 | — |
| 2-(2-methylaminoethoxy)-diphenylmethane hydrochloride | 0.00 | — |
| Amitriptyline | 1.00 | 65 |

Table II

| CNS Depressant, Anticonvulsant and Central anticholinergic Activity in Mice | | | | |
|---|---|---|---|---|
| Compound | Anticonvulsant activity ED50 (mg/kg i.p.) | Muscle Relaxant Action ED50 (mg/kg i.p.) | Spontaneous motor activity depression ED50 (mg/kg i.p.) | Antitremorine effect ED50 (mg/kg i.p.) |
| 2-(3-methylaminopropoxy)-diphenylmethane hydrochloride | 40 | 65 | 90 | 42 |
| Amitriptyline | 16 | 15 | 18 | 4 |

It will be apparent from Tables I and II that 2-(3-methylaminopropoxy)diphenylmethane exhibits lower toxicity, weaker CNS depressant and anticholinergic action at the same relative potency as compared with Amitryptyline.

The compounds of this invention can be administered by any means that effects palliating conditions of depression in warm-blooded animals.

For example, administration can be parenterally, subcutaneously, intravenously, intramuscularly or intraperitoneally. Alternatively or concurrently, administration can be by the oral route. The dosage administered will be dependent upon the age, health and weight of the recipient, the extent of depression, kind of concurrent treatment if any, frequency of treatment, and the nature of the effect desired. Generally, a daily dosage of active ingredient compound will be from about 0.5 to 50 mg per kg of body weight. Normally, from 1 to 30 mg per kg per day, in one or more applications per day is effective to obtain the desired result.

The compound of Formula I can be employed in dosage forms such as tablets, capsules, powder packets, or liquid solutions, suspensions, or elixirs, for oral administration, or sterile liquid formulations such as solutions or suspensions for parenteral use. In such compositions, the active ingredient will ordinarily always be present in an amount of at least 0.5% by weight based on the total weight of the composition and not more than 90% by weight.

Besides the active ingredient of this invention, the composition will contain a solid or liquid non-toxic pharmaceutical carrier for the active ingredient. In one embodiment of a composition, the solid carrier can be a capsule of the ordinary gelatin type. In the capsule is from about 30-60% by weight of a compound of Formula 1 and 70-40% of a carrier. In another embodiment, the active ingredient is tableted with or without adjuvants, or put into powder packets. These capsules, tablets and powders generally constitute from about 5% to about 95% and preferably from 25% to 90% by weight of active ingredient. These dosage forms preferably contain from about 5 to about 500 mg of active ingredient, with from about 25 to about 250 mg being most preferred.

The pharmaceutical carrier can be a sterile liquid such as water and oils, including those of petroleum, animal, vegetable or synthetic origin, such as peanut oil, soybean oil, mineral oil, sesame oil, or the like.

In general, water saline, aqueous dextrose and related sugar solutions, and glycols such as ethylene glycol, propylene glycol and polyethylene glycol are preferred liquid carriers, particularly for injectible solutions such as saline oridinarily contain from about 0.5% to 20% and preferably about 1 to 10% by weight of the active ingredient.

As mentioned above, oral administration can be in a suitable suspension or syrup, in which the active ingredient normally constitutes from about 0.5 to 10% by weight. The pharmaceutical carrier in such composition can be a watery vehicle such as an aromatic water, a syrup or a pharmaceutical mucilage.

Having generally described the invention, a more complete understanding can be obtained by reference to certain specific examples, which are included for purposes of illustration only and are not intended to be limiting unless otherwise specified.

EXAMPLE 1

A solution of 1.0 g 2-(3-bromopropoxy) diphenylmethane, 20 ml of 40% methylamine aqueous solution, and 100 ml of ethanol is allowed to stand at room temperature for 8 hours. Ethanol and excess methylamine are distilled in vacuo, 2N—NaOH aqueous solution is added, and the reaction product is extracted with ether. The ether solution is distilled, 2N—HCl solution is added and the solution is evaporated to dryness.

The residue is recrystallized from ethanol-ether to give 0.86 g (89% yield) of 2-(3-methylaminopropoxy) diphenylmethane hydrochloride, m.p. 148°–152° C.

Analysis — Calcd. for $C_{17}H_{21}NO \cdot HCl$ (percent): C, 69.97; H, 7.60; N, 4.80. Found (percent): C, 70.03; H, 7.40; N, 4.58.

EXAMPLE 2

Employing ethylamine instead of methylamine, Example 1 is repeated to give 2-(3-ethylaminopropoxy) diphenylmethane hydrochloride, m.p. 153°–154° C.

Analysis — Calcd. for $C_{18}H_{23}NO \cdot HCl$ (percent): C, 70.68; H, 7.91; N, 4.58. Found (percent): C, 70.69; H, 7.91; N, 4.48.

Having now fully described the invention, it will be apparent to one of ordinary skill in the art that many changes and modifications can be made thereto without departing from the spirit or scope of this invention as set forth herein.

What is claimed as new and intended to be covered by Letters Patent is:

1. A compound having the formula (I):

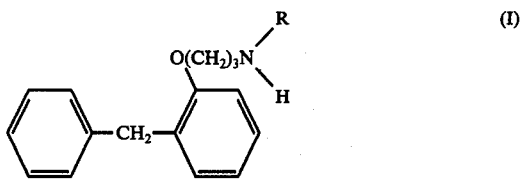

wherein R is $C_1$–$C_5$ alkyl.

2. The compound of claim 1, which is 2-(3-methylaminopropoxy)diphenylmethane.

3. The compound of claim 1, which is 2-(3-ethylaminopropoxy)diphenylmethane.

4. An antidepressant composition which comprises an antidepressant effective amount of a compound of claim 1 and a pharmaceutically acceptable carrier.

* * * * *